United States Patent [19]
Anton et al.

[11] Patent Number: 6,153,206
[45] Date of Patent: Nov. 28, 2000

[54] COSMETIC COMPOSITIONS

[75] Inventors: Waifong Liew Anton; Milan Bohuslay Bednarek, both of Wilmington, Del.; Joseph Frank Calello, Union, N.J.; Natividad Jose, Jamaica, N.Y.; Anjali Abhimanyu Patil; Julio Gans Russ, both of Westfield, N.J.; Robert Walter Sandewicz, Spotswood; Ann Marshall Ureneck, Red Bank, both of N.J.

[73] Assignee: Revlon Consumer Products Corporation, New York, N.Y.

[21] Appl. No.: 09/453,396

[22] Filed: Dec. 3, 1999

Related U.S. Application Data

[63] Continuation of application No. 08/918,136, Aug. 27, 1997.
[51] Int. Cl.[7] .............................. A61K 6/00; A61K 7/00; A61K 7/025; A61K 31/74
[52] U.S. Cl. ............................................ 424/401
[58] Field of Search .................... 424/64, 78.02, 424/78.17, 401

[56] References Cited

U.S. PATENT DOCUMENTS

| | | | |
|---|---|---|---|
| 5,468,477 | 11/1995 | Kumar et al. | 424/78.17 |
| 5,725,845 | 3/1998 | Krog et al. | 424/64 |
| 5,837,223 | 11/1998 | Barone et al. | 424/64 |

*Primary Examiner*—Thurman K. Page
*Assistant Examiner*—S. Howard
*Attorney, Agent, or Firm*—Julie Blackburn

[57] ABSTRACT

A cosmetic composition comprising an oil component and a particulate matter component, the improvement wherein the composition additionally contains an uncrosslinked synthetic polymer comprising a first repeat unit selected from the group consisting of methacrylate ester monomers which, if polymerized, would yield a polymer having a glass transition temperature of −10 to 75° C.; and a second repeat unit selected from the group consisting of methacrylate ester monomers which, if polymerized, would yield a polymer having a glass transition temperature in the range of about 76 to 120° C., the synthetic polymer having a glass transition temperature ranging from about 20 to 105° C.

19 Claims, No Drawings

COSMETIC COMPOSITIONS

This is a continuation of copending application Ser. No. 08/918,136, filed Aug. 27, 1997.

TECHNICAL FIELD

The invention is in the field of cosmetic compositions.

BACKGROUND OF THE INVENTION

Cosmetic compositions are generally defined as compositions suitable for application to the human body. Pigmented cosmetic compositions such as makeup, blush, lipstick, and eyeshadow are used to color the skin and lips, or to moisturize, hide wrinkles, and the like. Since color is one of the most important reasons for wearing cosmetics, color containing cosmetics must be very carefully formulated to provide maximum wear and effect.

Lipsticks are worn by most women. Generally if a woman wears any colored cosmetic composition at all it is lipstick. There are generally two types of lipstick. The first type is generally a combination of waxes, high viscosity oils, and pigments. These lipsticks provide varying degrees of shine and moisture to the lips due to the high oil content. However, these types of lipsticks are easily removed from the lips when the lips are touched with tissue, drinking vessels, tableware, or other skin surfaces. Thus, they must be frequently reapplied. The second type of lipsticks are the transfer resistant lipsticks such as those disclosed in U.S. Pat. No. 5,505,937, which is hereby incorporated by reference. Such lipsticks were commercially introduced several years ago. Transfer resistant lipsticks are generally comprised of some type of volatile solvent in place of at least a portion of the high viscosity oil, in addition to waxes, pigments and other ingredients. Transfer resistant lipsticks adhere extremely well to the lips and are not readily removed by eating, drinking, and the like. Thus, frequent reapplication is not necessary and the wearer can apply the lipstick and be sure that it will stay on for a substantial period of time before wearing off.

Interestingly enough, the majority of women prefer lipsticks that provide a shiny finish to the lips. Shine is believed by some to provide a very youthful appearance that is associated with health and well-being. However, in lipsticks, a shiny finish is always achieved with oils, in particular, high viscosity oils. It is not always desireable to incorporate shine-enhancing levels of oil into lipstick. Incorporating high amounts of oil in the standard non-transfer resistant lipsticks, at some point compromises stick structure and provides a very greasy feel on the lips. With respect to the transfer resistant lipsticks, incorporating shine-enhancing amounts of high viscosity oils compromises transfer resistance. Thus, it appears that shine is achieved at the expense of other desireable properties such as stick structure, feel on the lips, and transfer resistance.

Therefore, there is a need for a cosmetic stick composition such as lipstick, which provides a shiny finish on the lips and at the same time does not compromise feel, stick integrity, and transfer resistance.

It is an object of the invention to provide a cosmetic composition that provides a shiny finish on the skin.

It is an object of the invention to provide a lipstick composition that provides a shiny finish on the lips as well as excellent stick structure and suitable feel.

It is an object of the invention to provide a transfer resistant lipstick composition that provides a shiny finish on the lips without compromising transfer resistance.

It is an object of the invention to provide a method for improving the shine of a finish provided by a transfer resistant lipstick which is applied to the lips, comprising adding to the lipstick a shine enhancing effective amount of a polymer containing hard and soft portions.

SUMMARY OF THE INVENTION

The invention is directed to a cosmetic composition comprising an oil component and a particulate matter component, the improvement wherein the composition additionally contains an uncrosslinked synthetic polymer comprising:

(a) a first repeat unit selected from the group consisting of methacrylate ester monomers which, if polymerized, would yield a polymer having a glass transition temperature of −10 to 75° C.; and (b) a second repeat unit selected from the group consisting of methacrylate ester monomers which, if polymerized, would yield a polymer having a glass transition temperature in the range of about 76 to 120° C., said synthetic polymer having a glass transition temperature in the range of about 20 to 105° C.

DETAILED DESCRIPTION

The cosmetic compositions of the invention are cosmetics for application to the skin or lips. Preferably, the cosmetic compositions of the invention are in the form of sticks. The term "stick" refers to cosmetic compositions having a consistency such that they can be molded into the form of a stick—for instance by being heated until molten and then poured into a mold and cooled. Also included within the definition of "stick" are anhydrous compositions of the invention that are capable of being formed into sticks, but are poured into pans or other types of cake or cream forms to deliver certain consumer benefits. For example, an eyeshadow composition in accordance with the invention may be molded in the stick form, but it may be desired to pour it into a pan because this container is more desireable from a consumer standpoint. Preferably, the cosmetic sticks of the invention are anhydrous, although they may contain varying amounts of water. The term "anhydrous" means that the composition contains no more than about 5 percent, more particularly about 1 to 2 percent by weight or less of water, or more preferably, that water is not intentionally added to the cosmetic composition of the invention. All percentages mentioned herein are percentages by weight unless otherwise indicated. All percentages stated herein are percentages by weight unless otherwise indicated.

The Polymer

The polymer of the invention comprises portions having a low glass transition temperature and portions having a high glass transition temperature, in other words a polymer with "hard" and "soft" portions. Without being bound by this explanation, it is believed that the soft portion of the polymer provides a flexibile film in the compositions of the invention, while the hard portion of the polymer aids providing shine to the film. The polymer of the invention may be a copolymer, a terpolymer, block copolymer, or graft copolymer, or have any number of different units provided it contains the first and second repeat units as identified herein.

The term "glass transition temperature" means the temperature at which an amorphous material such as glass or a high polymer changes from a brittle, vitreous state to a plastic state. With respect to methacrylates, the glass transition temperature generally correlates with the number of carbon atoms in the ester group, i.e. the greater the number of carbon atoms the lower the glass transition temperature. The glass transition temperature of copolymers may be theoretically calculated according to the following formula:

$$\frac{1}{Tg} = \frac{W_1}{Tg_1} + \frac{W_2}{Tg_2} + \frac{W_3}{Tg_3} + \cdots \frac{W_n}{Tg_n}$$

where Tg is the glass transition temperature of the polymer in degrees Kelvin; $W_1$, $W_2$, $W_3$ . . . $W_n$ are the weight fractions of each of the components of the polymer, and $Tg_1$, $Tg_2$, $Tg_3$, and $Tg_n$ are the Tg in degrees Kelvin, of the homopolymer having a molecular weight average of about 20,000 made from the individual monomer units of the polymer [Reference: T. G. Fox, Bull. Am. Phys. Soc., No. 3, page 123 (1956)]. A more practical way to measure Tg is by differential scanning calorimetry (DSC), which measures the change in the enthalpy of a polymer with temperature. Preferably, the Tg of copolymers used in the compositions of the invention are measured by DSC.

The term "repeat unit" means a monomer unit of the polymer which is present more than one time in the polymer chain, and it can be present in either repetitive sequence or in random sequence with the other monomer units.

The compositions of the invention comprise 0.1–60%, preferably 1–40%, more preferably 3–30% of an uncrosslinked synthetic polymer comprising a first repeat unit selected from group consisting of methacrylate ester monomers which, if polymerized, would yield a polymer having a glass transition temperature ranging from about −10 to 75° C.; and a second repeat unit selected from the group consisting of methacrylate ester monomers which, if polymerized, would yield a polymer having a glass transition temperature ranging from about 76 to 120° C.; wherein the synthetic polymer has a glass transition temperature of 20 to 105° C. Preferably, the first repeat unit comprises at least one methacrylate ester monomer which, if polymerized to a molecular weight average of about 20,000, would yield a polymer having a glass transition temperature in the range of about −10 to 75° C. Preferably the second repeat unit comprises at least one methacrylate ester monomer which, if polymerized to a molecular weight average of about 20,000 would yield a polymer having a glass transition temperature in the range of about 76 to 120° C. The final polymer may contain, in addition to the first and second repeat units, other monomeric units such as styrene, ethylenically unsaturated monomer units such as ethylene, propylene, butylene, etc., vinyl monomers such as vinyl chloride, styrene, silicon repeat units, and so on, provided that the final polymer has at least one first repeat unit having a glass transition temperature ranging from about −10 to 75° C., and at least one second repeat unit having a glass transition temperature ranging from about 76 to 120° C., wherein the final polymer has a glass transition temperature ranging from about 20 to 105° C.

A variety of methacrylate ester monomers are suitable for use as first repeat unit. Preferably, the methacrylate ester monomers are aliphatic esters of methacrylic acid, such as is obtained with the esterification of methacrylic acid with an aliphatic alcohol of 2 to 30, preferably 2 to 20, more preferably 2 to 8 carbon atoms. If desired the aliphatic alcohol may have one or more hydroxy groups. Preferably the first repeat unit comprises isobutylmethacrylate, n-butylmethacrylate, hydroxyethylmethacrylate, ethylhexylmethacrylate, and the like.

A variety of monomers are suitable for use as the second repeat unit. Preferably the second repeat unit is methacrylic acid esterified with an aliphatic alcohol of 1 to 30 carbon atoms or an unsaturated camphene ring. More preferably the second ethylenically unsaturated monomer is isobornyl methacrylate or methylmethacrylate.

Preferably, the first and second repeat units each independently have the following general formula:

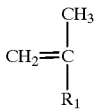

wherein $R_1$ is COOM wherein M is a substituted or unsubstituted $C_{1-30}$ straight or branched chain alkyl where the substitutents are halogen or alkoxy; pyrrolidone; or a substituted or unsubstituted aromatic, cyclic, alicylic, or bicyclic ring where the substitutents are $C_{1-30}$ straight or branched chain alkyl or halogen.

Preferably, in first repeat unit $R_1$ is COOM where M is $C_{1-30}$ alkyl, more preferably M is a $C_{1-10}$ alkyl, more preferably M is a $C_{1-5}$ alkyl, and most preferably M is a $C_4$ branched chain alkyl, or isobutyl.

Preferably, in the second repeat unit, $R_1$ is COOM where M is H or $C_{1-30}$ alkyl or a alicyclic or bicyclic ring, more preferably $R_1$ is COOM where M is a $C_{1-5}$ alkyl or an alicyclic ring, and most preferably $R_1$ is COOM where M is $CH_3$ or an alicyclic ring which is isobornyl.

Some types of polymers in accordance with the invention include, but are not limited to, those illustrated below, with the first and second repeat units being selected from the groups set forth:

| First repeat unit: | Tg ° C. | Second repeat unit: | Tg ° C. |
|---|---|---|---|
| I = isobutyl methacrylate | 53 | M = methylmethacrylate | 105 |
| E = ethylmethacrylate | 65 | B = isobornyl methacrylate | 105 |
| X = hexyl methacrylate | −5 | | |

Block copolymer:

MMMIIMMMIIIMMMIII
Random copolymer:

IMMMIMIMMMMIMMIIMMMIMIIIMMIMMIII
Block terpolymer:

IIIMMMEEEIIIMMMEEEIIIMMMEEEIIIMMMEEE
Random terpolymer:

IMEEMIIEEMMIEMIMEEMIIMMEIMMEI
Graft copolymer:

IIIIIIIIIIIIIBBBBBBBBBB, or
EMEMEEMEMEEMMEMEEEMEEMMEMMEE
B        B        B
B        B        B
B        B        B
B                B
B
Graft terpolymer:

IIIIIIIIIIIBBBBBBBBBBMMMMMMMM
Random polymer:

IMEXBBBXEMIMEBIXMBIXEMEIXB

In the copolymers of the invention, preferably the first repeat unit if, polymerized to a molecular weight average of about 20,000 has a glass transition temperature of about 0–70° C., more preferably 20–65° C., and the second repeat unit, if polymerized to a molecular weight of about 20,000, has a glass transition temperature of about 80–115° C., more preferably 90–110° C.; and the final copolymer has a glass transition temperature of about 20–105° C., preferably 45–104° C. Generally, the weight portions of the first and second repeat units in the copolymer can vary from 2–99% by weight of the first repeat unit to 1–98% by weight of the second repeat unit, and vice versa, for example, as set forth below:

| % isobornylmethacrylate | % isobutylmethacrylate | Tg ° C. |
|---|---|---|
| 98 | 2 | 104 |
| 95 | 5 | 102 |
| 90 | 10 | 99 |
| 80 | 20 | 93 |
| 60 | 40 | 82 |
| 50 | 50 | 77 |
| 1 | 99 | 53 |

Preferably the first repeat unit comprises from about 5–95%, preferably 20–80%, more prefereably 40–60% by weight of the polymer, and the second repeat unit comprises from about 5–95%, preferably 20–80%, more preferably 40-60% by weight of the polymer. Preferably the polymer contains about 50% by weight of the first repeat unit and 50% by weight of the second repeat unit, has a glass transition temperature of about 77° C., and a molecular weight average of 5,000 to 300, 000, preferably 5,000 to 50,000. Most preferably, the preferred polymer of the invention is a copolymer comprising a 50/50 ratio of isobutyl methacrylate and isobornyl methacrylate, which has a glass transition temperature of about 77° C., and a molecular weight of to 50,000.

Examples of monomer units which may be used to make the copolymers in accordance with the invention include those set forth below:

| First repeat unit | Tg ° C. homo-polymer | Second Repeat Unit | Tg ° C. homo-polymer |
|---|---|---|---|
| isobutyl methacrylate | 53 | methyl methacrylate | 105 |
| pentyl methacrylate | −5 | phenyl methacrylate | 105 |
| 2-methoxyethyl-methacrylate | 13 | isopropyl methacrylate | 81 |
| | | isobornyl methacrylate | 105 |
| propylmethacrylate | 35 | chloroethylmethacrylate | 103 |
| hexylmethacrylate | −5 | | |
| fluoromethylacrylate | 15 | | |
| 2-ethylhexylmethacrylate | −10 | | |
| ethylmethacrylate | 65 | | |
| glycidyl methacrylate | 46 | | |
| hexadecylmethacrylate | 13 | | |
| pentylmethacrylate | −5 | | |
| 1,1,1-trifluoroisopropyl-methacrylate | 66 | | |

The polymers used in the compositions of the invention can be prepared by conventional free radical polymerization techniques in which the monomers, solvent, and polymerization initiator are charged over a 1–24 hour period of time, preferably 2–8 hours, into a conventional polymerization reactor in which the constituents are heated to about 60–175° C., preferably 80–100° C. The polymers may also be made by emulsion polymerization or suspension polymerization using conventional techniques. Also Anionic or Group Transfer Polymerization (GTP) is another method by which the polymers used in the invention may be made. GTP is well known in the art and disclosed in U.S. Pat. Nos. 4,414,372; 4,417,034; 4,508,880; 4,524,196; 4,581,428; 4,588,795; 4,598,161; 4,605,716; 4,605,716; 4,622,372; 4,656,233; 4,711,942; 4,681,918; and 4,822,859; all of which are hereby incorporated by reference. Preferably, the copolymers used in the compositions of the invention are made by GTP in accordance with the procedures set forth in U.S. Pat. Nos. 4,588,795 and 4,605,716.

Oil

The compositions of the invention contain 1–60%, preferably 10–50%, more preferably 10–40% oil. The oils used may be volatile or nonvolatile. The term "volatile" means that the oil has a measureable vapor pressure, or a vapor pressure of at least 2 mm. of mercury at 20° C. The term "nonvolatile" means that the oil has a vapor pressure of less than 2 mm. of mercury at 20°C. If the cosmetic compositions of the invention are transfer resistant sticks, it is desireable to use significant amounts of volatile solvent for the oil component. Suitable volatile solvents or oils are liquids, and enable easy formulation of the cosmetic stick of the invention. When the cosmetic stick product of the invention is applied to skin or lips, the volatile solvent of the invention must be capable of flashing off to leave the other ingredients in the stick on the skin. Suitable volatile solvents generally have a viscosity of 0.5 to 10 centistokes at 25° C. Suitable volatile oils include linear silicones, cyclic silicones, paraffinic hydrocarbons, or mixtures thereof.

Cyclic silicones (or cyclomethicones) are of the general formula:

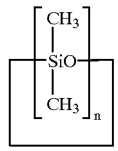

where n=3–7.

Linear volatile silicones in accordance with the invention have the general formula:

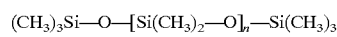

where n=0–7, preferably 0–5.

Linear and cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, hexamethyldisiloxane, and mixtures thereof.

Also suitable as the volatile oils are various straight or branched chain paraffinic hydrocarbons having 5 to 40 carbon atoms, more preferably 8-20 carbon atoms. Suitable hydrocarbons include pentane, hexane, heptane, decane, dodecane, tetradecane, tridecane, and C8-20 isoparaffins as disclosed in U.S. Pat. No. 3,439,088 and 3,818,105, both of which are hereby incorporated by reference. Preferred volatile paraffinic hydrocarbons have a molecular weight of 70–225, preferably 160 to 190 and a boiling point range of 30 to 320, preferably 60–260 degrees C., and a viscosity of less than 10 cs. at 25 degrees C. Such paraffinic ydrocarbons are available from EXXON under the ISOPARS trademark, and from the Permethyl Corporation. Suitable $C_{12}$ isoparaffins are manufactured by Permethyl Corporation under the tradename Permethyl 99A. Another $C_{12}$ isoparaffin (isododecane) is distributed by Presperse under the tradename Permethyl 99A. Various $C_{16}$ isoparaffins commercially available, such as isohexadecane (having the tradename Permethyl R), are also suitable. Transfer resistant cosmetic sticks of the invention will generally comprise a mixture of volatile silicones and volatile paraffinic hydrocarbons.

A wide variety of nonvolatile oils are also suitable for use in the cosmetic compositions of the invention. The nonvolatile oils generally have a viscosity of greater than 10 centipoise at 25° C., and may range in viscosity up to 1,000,000 centipoise at 250° C. Examples of nonvolatile oils suitable for use in the cosmetic sticks of the invention include esters of the formula RCO—OR' wherein R and R' are each independently a $C_{1-25}$, preferably a $C_{4-20}$ straight or branched chain alkyl, alkenyl or alkoxycarbonylalkyl or alkylcarbonyloxyalkyl. Examples of such esters include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, cocodicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, and fatty alcohols such as oleyl alcohol, isocetyl alcohol, and the like, as well as the esters disclosed on pages 24–26 of the *C.T.F.A. Cosmetic Ingredient Handbook*, First Edition, 1988, which is hereby incorporated by reference.

The oil may also comprise naturally occuring glyceryl esters of fatty acids, or triglycerides. Both vegetable and animal sources may be used. Examples of such oils include castor oil, lanolin oil, triisocetyl citrate, $C_{10-8}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, and the like.

Also suitable as the oil are synthetic or semi-synthetic glyceryl esters, e.g. fatty acid mono-, di-, and triglycerides which are natural fats or oils that have been modified, for example, acetylated castor oil, glyceryl stearate, glyceryl dioleate, glyceryl distearate, glyceryl trioctanoate, glyceryl distearate, glyceryl linoleate, glyceryl myristate, glyceryl isostearate, PEG castor oils, PEG glyceryl oleates, PEG glyceryl stearates, PEG glyceryl tallowates, and so on.

Also suitable as the oil are nonvolatile hydrocarbons such as isoparaffins, hydrogenated polyisobutene, mineral oil, squalene, petrolatum, and so on.

Straight or branched chain fatty alcohols having the formula R—OH, wherein R is a straight or branched chain saturated or unsaturated alkyl having 6–30 carbon atoms, are also suitable oils. Such fatty alcohols include cetyl alcohol, stearyl alcohol, cetearyl alcohol, and the like.

Also suitable as the oil are various lanolin derivatives such as acetylated lanolin, acetylated lanolin alcohol, and so on.

Nonvolatile silicones, both water soluble and water insoluble, are also suitable as the oil component. Such silicones preferably have a viscosity of 10 to 600,000 centistokes, preferably 20 10 to 100,000 centistokes at 250° C. Suitable water insoluble silicones include amodimethicone, bisphenylhexamethicone, dimethicone, hexadecyl methicone, methicone, phenyl trimethicone, simethicone, dimethylhydrogensiloxane, stearoxytrimethylsilane, vinyldimethicone, and mixtures thereof. Also suitable are water soluble silicones such as dimethicone copolyol, dimethiconol, and the like. Such silicones are available from Dow Corning as the 3225C formulation aid, Dow 190 and 193 fluids, or similar products marketed by Goldschmidt under the ABIL tradename.

Also suitable as the nonvolatile oil are various fluorinated oils such as fluorinated silicones, fluorinated esters, or perfluropolyethers. Particularly suitable are fluorosilicones such as trimethylsilyl endcapped fluorosilicone oil, polytrifluoropropylmethylsiloxanes, and similar silicones such as those disclosed in U.S. Pat. No. 5,118,496 which is hereby incorporated by reference. Perfluoropolyethers like those disclosed in U.S. Pat. Nos. 5,183,589, 4,803,067, 5,183,588 all of which are hereby incorporated by reference, which are commercially available from Montefluos under the trademark Fomblin, are also suitable shine enhancers.

Guerbet esters are also suitable oils. The term "guerbet ester" means an ester which is formed by the reaction of a guerbet alcohol having the general formula:

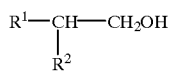

with a carboxylic acid having the general formula:

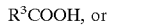

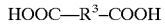

wherein $R^1$ and $R^2$ are each independently a $C_{4-20}$ alkyl and $R^3$ is a substituted or unsubstituted fatty radical such as a $C_{1-50}$ straight or branched chain saturated or unsaturated alkyl or alkylene, or phenyl, wherein the substituents are halogen, hydroxyl, carboxyl, and alkylcarbonylhydroxy. Particularly preferred is a carboxylic acid wherein the R group is such to provide an ingredient known as meadowfoam seed oil.

Preferably, the guerbet ester is a fluoro-guerbet ester which is formed by the reaction of a guerbet alcohol and carboxylic acid (as defined above), and a fluoroalcohol having the following general formula:

wherein n is from 3 to 40.

Examples of suitable fluoro guerbet esters are set forth in U.S. Pat. No. 5,488,121 which is hereby incorporated by reference. Suitable fluoro-guerbet esters are also set forth in U.S. Pat. No. 5,312,968 which is hereby incorporated by reference. Most preferred is a guerbet ester having the tentative CTFA name fluoro-octyldodecyl meadowfoamate. This ester is sold by Siltech. Norcross Georgia as Developmental Ester L61 125A, under the tradename Silube GME-F.

Preferably, the compositions of the invention contain a mixture of volatile and nonvolatile oils, so that the amount of volatile oil is about 1–50%, preferably 540%, more preferably 10–30% by weight of the total composition, and the amount of nonvolatile oil is about 1–50%, preferably 5–40%, more preferably 10–30% by weight of the total composition. In the preferred embodiment of the invention, the volatile oils are cyclomethicone and isododecane, and the preferred nonvolatile oil is dimethicone and fluoro octyldodecylmeadowfoamate.

Particulate Matter

The composition of the invention may contain 1–50%, preferably 7–45%, more preferably 10–40%, by weight of the total composition, of particulate matter having a particle size of 0.02 to 100, preferably 0.5 to 100, microns. The particulate matter may be colored or non-colored (for example white). Suitable particulates include bismuth oxychloride, titanated mica, fumed silica, spherical silica, polymethylmethacrylate, polyethylene, polypropylene, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone oil or various other agents either alone or in combination, which coat the powder surface and render the particles more lipophilic in nature.

The particulates may also include various organic and inorganic pigments. The organic pigments are generally various aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes, in particular the Lakes of D&C and FD&C colors. Inorganic pigments include iron oxides, ultramarines, chromium, chromium hydroxide colors, and mixtures thereof.

Preferably the composition will contain both pigmented and non-pigmented particulates. Obviously the percentage of pigments used in the particulate phase will depend on the type of cosmetic being formulated. Color cosmetics generally have a much higher concentration of color than other types of cosmetics. Generally the weight ratio of pigmented to non-pigmented particulates range from 1:50 to 50:1. It should be noted that particulates that are white or have no color are considered non-pigmented particulates in accordance with the invention, while particulates which exhibit color other than white are considered pigmented particulates in accordance with the invention.

Other Ingredients

Wax

Preferably, the cosmetic compositions of the invention generally contain from about 1–70%, preferably 1–30%, more preferably 1–25% by weight of a cosmetically acceptable natural or synthetic wax. The waxes that can be used are solid or semi-solid waxes having a melting point of 30 to 120° C. and generally includes animal waxes, plant waxes, mineral waxes, silicone waxes, synthetic waxes, and petroleum waxes.

Examples of waxes in accordance with the invention include bayberry, beeswax, candelilla, carnauba, ceresin, cetyl esters, hydrogenated jojoba oil, hydrogenated jojoba wax, hydrogenated microcrystalline wax, hydrogenated rice bran wax, japan wax, jojoba butter, jojoba esters, jojoba wax, lanolin wax, microcrystalline wax, mink wax, montan acid wax, montan wax, ouricury wax, ozokerite, paraffin, PEG-6 beeswax, PEG-8 beeswax, rice bran wax, shellac wax, spent grain wax, sulfurized jojoba oil, synthetic beeswax, synthetic candelilla wax, synthetic carnauba wax, synthetic japan wax, synthetic jojoba oil, synthetic wax, stearoxy dimethicone, dimethicone behenate, stearyl dimethicone, and the like, as well synthetic homo- and copolymer waxes from the ethylene series. In the preferred embodiment of the invention the waxes are polymers of ethylene and/or propylene.

Preferably, the composition of the invention contain fluorinated waxes, either alone or in addition to the above-mentioned natural or synthetic waxes. Particularly preferred are fluorinated dimethicone copolyols disclosed in U.S. Pat. No. 5,446,114, which is hereby incorporated by reference, having the general formula:

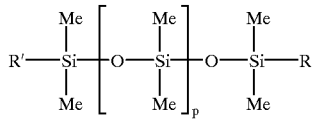

wherein:

p is an integer ranging from 1 to 2,000;

Me is methyl;

R' is $-(CH_2)_3O-(EO)_a-(PO)_b-(EO)_cH$;

R is $-(CH_2)_2-((CF_2)_sCF_3$;

s is an integer ranging from 1 to 13;

a, b, and c are each independently integers ranging from 0 to 20;

EO is $-(CH_2CH_2-O)$; and

PO is $-(CH_2CH(CH_3)O-$.

Particularly prefered is a compound, dimethiconol fluoroalcohol dilinoleic acid, which is sold by Siltech, Inc., under the tradename Silwax F.

Shine Enhancers

It may be desireable to include other ingredients in the formulation, in particular certain ingredients which enhance shine of the finish provided by the cosmetic composition of the invention. About 5–60%, preferably 5–50%, more preferably 745% of shine enhancers are suggested. Examples of shine enhancing ingredients are homo- or copolymers which are clear, or in other words have an index of refraction of 1.5 or greater. Examples of clear polymers are alkylated polyvinylpyrrolidones sold by International Specialty Products under the GANEX tradename. These polymers are copolymers of vinylpyrrolidone and long chain alpha olefins, and have the following general formula:

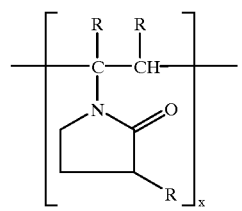

wherein R is H or a $C_{1-40}$ straight or branched chain alkyl, preferably a $C_{6-22}$ straight or branched chain alkyl. Examples of such polymers are disclosed in U.S. Pat. Nos. 4,514,271, 3,423,381, 3,423,381, and 3,417,054, all of which are hereby incorporated by reference. The composition preferably comprises 0.5–35%, preferably 1–20%, more preferably 1–15% of a $C_{6-22}$ alkylated polyvinylpyrrolidone. Particularly preferred are PVP/eicosene copolymer and PVP/hexadecene copolymer, and in particular PVP/eicosene copolymer.

Also suitable are polyvinylpyrrolidone (PVP) homopolymers, which may be purchased from International Special Products under the PVP-K tradename, in particular PVP K-15, PVP K-30, PVP K-60, PVP K-90, PVP K-120.

PVP/acetate copolymers, which are copolymers of vinylpyrrolidone and vinylacetate, are also suitable shine enhancers. Such polymers are sold under the PVP/VA tradename by International Specialty Products.

Also suitable shine enhancers are monoalkyl esters of poly(methylvinyl etherimaleic acid), which are sold by International Specialty Products under the GANTREZ tradename.

It may also be desired to add other ingredients such as preservatives, antioxidants, vitamins, emulsifiers, and the like.

The preferred cosmetic compositions of the invention are cosmetic sticks comprising:

3–30% of the copolymer,

10–40% of a volatile oil, preferably cyclomethicone, a volatile paraffinic hydrocarbon, or mixtures thereof;

10–30% of a nonvolatile oil, preferably dimethicone, fluoro guerbet ester, or mixtures thereof;

1–30% of a wax having a melting point of 30 to 120° C., preferably a synthetic wax which is an aliphatic hydrocarbon, a fluorinated wax, or mixtures thereof; and 10–40% particulate matter having a particle size of 0.5 to 100 microns.

Most preferably, the composition additionally contains 7–45% shine enhancers, preferably one or more homo- or copolymers having an index of refraction of 1.5 or greater.

The invention will be further described in connection with the following examples which are set forth for the purpose of illustration only.

EXAMPLE 1

A shiny transfer resistant lipstick was made as follows:

|  | w/w % | |
| --- | --- | --- |
|  | A | B |
| Fluoro octyldodecyl meadowfoamate | 8.00 | 6.00 |
| Polydimethylsiloxane | 8.00 | 12.00 |
| Dimethiconol fluorodilinoleate | 8.00 | — |
| Polydecene | — | 1.00 |
| D&C Red Calcium Lake | 12.00 | 0.60 |
| Black iron oxide | — | 0.45 |
| FD&C yellow #5 Aluminum lake | — | 0.35 |
| Red iron oxide | — | 1.36 |
| Synthetic wax | 7.00 | 7.40 |
| Polyethylene | 0.80 | — |
| PVP/Eicosene copolymer | 8.00 | 8.00 |
| Isododecane | 6.00 | 5.00 |
| Copolymer solution* | 19.00 | 20.00 |
| Mica, silica | 5.00 | 1.20 |
| Cyclomethicone/trimethylsiloxy silicate | 15.00 | 11.00 |
| Cyclomethicone | 3.20 | 5.25 |
| Propyl paraben | — | 0.10 |
| BHA | — | 0.10 |
| Diisostearoyl trimethylolpropane siloxy silicate | — | 1.00 |
| Cetyl dimethicone copolyol/polyglyceryl-4-isostearate/hexyl laurate** | — | 8.04 |
| Ethylene brassylate | — | 0.10 |
| Fragrance | — | 0.05 |
| Bismuth oxychloride/mica | — | 7.00 |
| Titanium dioxide/mica/iron oxides | — | 4.00 |

*A solution containing about 90 parts by weight of a copolymer containing about equal parts by weight of isobutyl methacrylate and isobornyl methacrylate and about 10 parts by weight of isododecane.
**ABIL WE-09: A mixture of 33% cetyl dimethicone copolyol, 34% polyglyceryl-4-isostearate, and 33% hexyl laurate.

The copolymer solution was made by by GTP polymerization of the monomer units in sododecane solvent in accordance with the procedures set forth in U.S. Pat. Nos. 4,588,791 and 605,716. The polymer had a molecular weight of 27,100.

The lipstick composition was made by mixing the solid, semi-solid and oil ingredients with heat. The pigments, powders, and other ingredients were added. The compositions were poured into molds and allowed to cool.

EXAMPLE 2

A moisturizing, long lasting (but not transfer resistant) lipstick was made according to the following formula:

|  | w/w % |
| --- | --- |
| Synthetic wax | 8.50 |
| Paraffin wax | 2.00 |
| Triisostearyl citrate | 36.40 |
| Dimethicone | 1.40 |
| Cholesteryl/lanasterol | 1.00 |
| Red iron oxides | 3.54 |
| D&C Red #7 Calcium Lake | 0.78 |
| FD&C Yellow #5 Aluminum Lake | 1.55 |
| Black iron oxides | 1.76 |
| Titanium dioxide | 2.37 |
| Lanolin oil | 20.30 |
| Moisturizing complex* | 0.25 |
| Phytosterol/octyldodecyl/lauryl glutamate | 0.05 |
| Cyclomethicone | 20.00 |
| Copolymer solution** | 0.10 |

**A solution containing about 90 parts by weight of a copolymer containing about equal parts by weight of isobutyl methacrylate and isobornyl methacrylate and about 10 parts by weight of isododecane.
*Moisturizing complex:

|  | w/w % |
| --- | --- |
| Bis-diglyceryl polyacyladipate | 15.00 |
| Methyl glucose sesqistearate | 27.00 |
| Hydrogenated polyisobutene | 23.70 |
| Sodium PCA | 2.00 |
| Gingko extract | 1.00 |
| Sodium lactate/sodium PCA/urea/hydrolyzed collagen/sodium phosphate | 1.00 |
| Methyl paraben | 0.30 |
| Propyl paraben | 0.10 |
| Isocetyl stearate | 11.90 |
| Sodium hylauronate/hydrolyzed glycosaminoglycans | 9.00 |
| Magnesium ascorbyl phosphate | 0.50 |
| Pseudoceramide (Questamide H) | 1.00 |
| Acrylates copolymer | 7.50 |

The copolymer solution was made as set forth in Example 1, above.

The lipstick composition was made by combining the synthetic wax, paraffin wax, triisostearyl citrate, dimethicone, and cholesteryl lanasterol with heat to cause the waxes to melt. The pigments, lanolin oil, moisturizing complex and phytosterol mixture was then added with stirring to mix the ingredients. They cyclomethicone and copolymer were added last. The mixture was poured into molds and allowed to cool to room temperature.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

What is claimed is:

1. A cosmetic composition comprising an oil component and a particulate matter component, the improvement wherein the composition additionally contains an uncrosslinked synthetic polymer consisting of polymerized ethylenically unsaturated monomers A and B, wherein:

(a) A is selected from the group consisting of methacrylate ester monomers which, if polymerized, would yield a polymer having a glass transition temperature of −10 to 75° C.; and (b) B is selected from the group consisting of methacrylate ester monomers which, if polymerized, would yield a polymer having a glass transition temperature in the range of about 76 to 120° C., said synthetic polymer having a glass transition temperature in the range of about 20 to 105° C.

2. The composition of claim 1 wherein the polymer contains two or more different A monomers.

3. The composition of claim 1 wherein the polymer contains two or more different B monomers.

4. The composition of claim 1 wherein the A and B monomers, if polymerized to a molecular weight average of 20,000 would yield polymers having a glass transition temperature of −10 to 75° C., and 76 to 120° C., respectively.

5. The composition of claim 1 wherein the A monomer is selected from the group consisting of methacrylic acid esters.

6. The composition of claim 5 wherein the A monomer is an aliphatic ester of methacrylic acid.

7. The composition of claim 6 wherein the A monomer is methacrylic acid esterified with an aliphatic alcohol of 2 to 8 carbon atoms.

8. The composition of claim 7 wherein the aliphatic alcohol has 1 or 2 hydroxy groups.

9. The composition of claim 6 wherein the A monomer is selected from the group consisting of isobutylmethacrylate, n-butylmethacrylate, hydroxyethylmethacrylate, and ethylhexylmethacrylate, and mixtures thereof.

10. The composition of claim 1 wherein the B monomer is a methacrylic acid ester.

11. The composition of claim 10 wherein the B monomer is methacrylic acid esterified with an aliphatic alcohol of 1 to 22 carbon atoms.

12. The composition of claim 10 wherein the B monomer is selected from the group consisting of isobornylmethacrylate, methylmethacrylate, and mixtures thereof.

13. The composition of claim 1 wherein the oil comprises both a volatile solvent having a viscosity of 0.5 to 10 centistokes at 25° C. and a nonvolatile oil having a viscosity of greater than 10 centistokes at 25° C.

14. The composition of claim 13 wherein the volatile solvent comprises one or more compounds selected from the group consisting of cyclomethicones of up to 7 silicon atoms, linear dimethicone of up to 9 silicon atoms, and straight or branched chain paraffinic hydrocarbons having about 5 to 40 carbon atoms.

15. The composition of claim 1 wherein the nonvolatile oil comprises one or more compounds selected from the group consisting of silicones, fatty alcohols, fatty esters, and nonvolatile hydrocarbon oils.

16. The composition of claim 15 wherein the nonvolatile oil comprises one or more compounds selected from the group consisting of dimethicone and a fluoro guerbet ester.

17. The composition of claim 1 additionally comprising 1–70% of a wax having a melting point of 30 to 120° C.

18. The composition of claim 17 wherein the wax is one or more compounds selected from the group consisting of an aliphatic hydrocarbon and a fluorinated silicone.

19. The composition of claim 1 which is an anhydrous stick.

* * * * *